US008235924B2

(12) United States Patent
Bachmann et al.

(10) Patent No.: US 8,235,924 B2
(45) Date of Patent: Aug. 7, 2012

(54) ORTHOTIC BRACE

(75) Inventors: Richard Bachmann, Cleveland, OH (US); Ronald Triolo, Cleveland Heights, OH (US); Arkady Polinkovsky, Cleveland, OH (US); Nicole Kern, Cleveland Heights, OH (US); Roger D. Quinn, Akron, OH (US); Rudolf Kobetic, Rocky River, OH (US)

(73) Assignee: Case Western Reserve University, Cleveland, OH (US)

( * ) Notice: Subject to any disclaimer, the term of this patent is extended or adjusted under 35 U.S.C. 154(b) by 142 days.

(21) Appl. No.: 12/761,945

(22) Filed: Apr. 16, 2010

(65) Prior Publication Data
US 2010/0268137 A1 Oct. 21, 2010

Related U.S. Application Data

(60) Provisional application No. 61/169,957, filed on Apr. 16, 2009, provisional application No. 61/170,003, filed on Apr. 16, 2009.

(51) Int. Cl.
*A61F 5/00* (2006.01)

(52) U.S. Cl. .............................. 602/16; 602/23; 602/27
(58) Field of Classification Search ................... 602/16, 602/23, 26–27; 128/878–879, 882
See application file for complete search history.

(56) References Cited

U.S. PATENT DOCUMENTS

| 6,872,187 | B1 * | 3/2005 | Stark et al. ..................... 602/16 |
| 2004/0153015 | A1 * | 8/2004 | Seligman et al. ............... 602/16 |
| 2005/0245853 | A1 * | 11/2005 | Scorvo .......................... 602/16 |
| 2007/0135745 | A1 * | 6/2007 | Seligman et al. ............... 602/16 |

* cited by examiner

*Primary Examiner* — Michael A. Brown
(74) *Attorney, Agent, or Firm* — Tarolli, Sundheim, Covell & Tummino LLP

(57) ABSTRACT

An orthotic brace (30) for a joint includes a bracing device (40) having first and second portions (42, 44) movable relative to one another and a mechanism (100) for placing the bracing device (40) in a first condition in which the first portion (42) has a first resistance to movement relative to the second portion (44) and a second condition in which the first portion (42) has a second, different resistance to movement relative to the second portion (44). The mechanism (100) is capable of placing the bracing device (40) in a third condition in which the first portion (42) has a third resistance to movement relative to the second portion (44) that is between the first and second resistance.

21 Claims, 11 Drawing Sheets

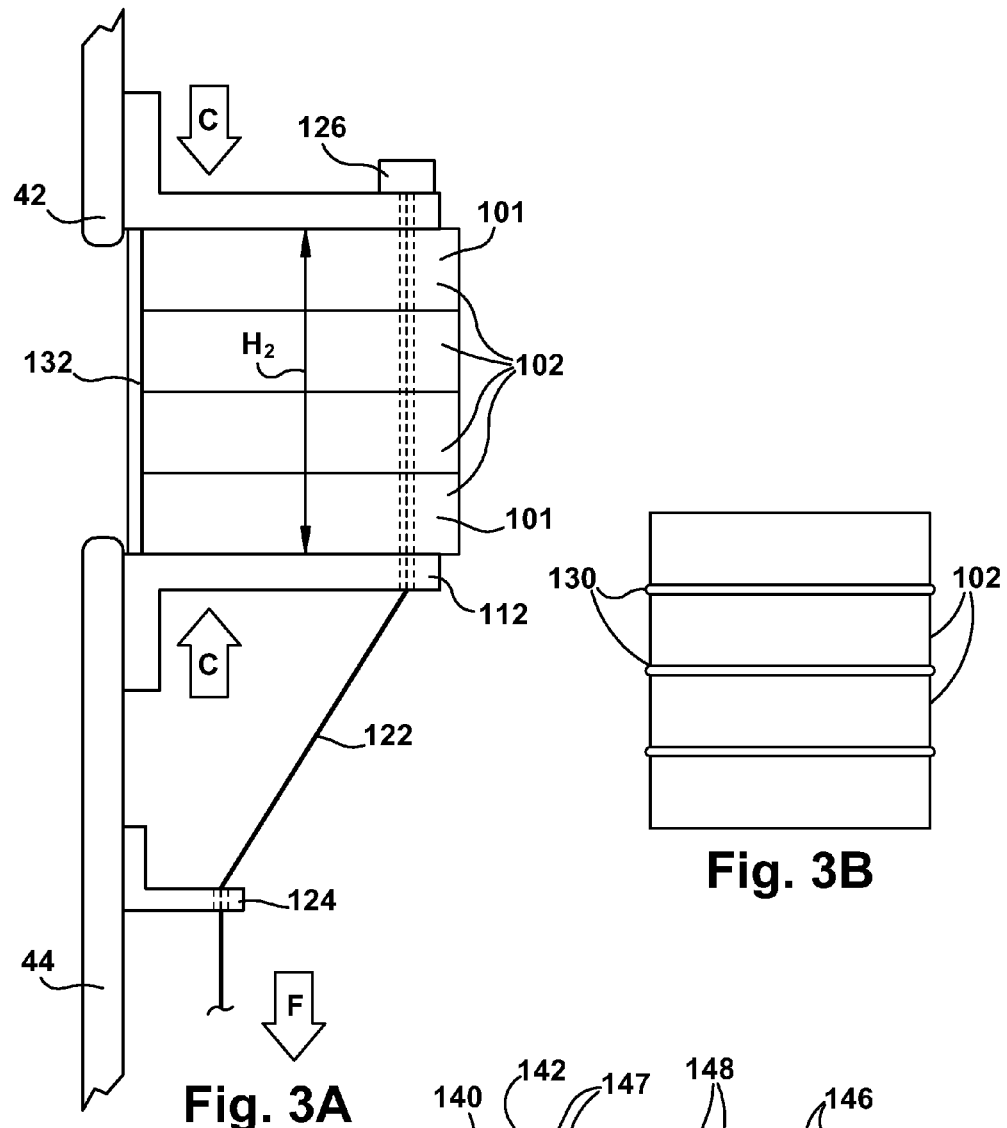
Fig. 3A
Fig. 3B
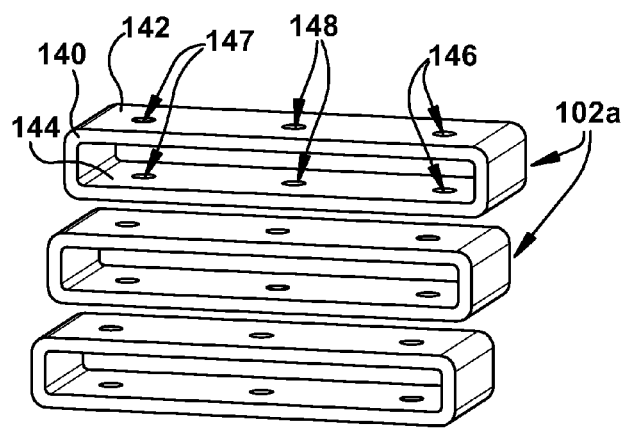
Fig. 4A

ORTHOTIC BRACE

RELATED APPLICATION

This application claims priority from U.S. Provisional Application Nos. 61/169,957, filed Apr. 16, 2009 and 61/170,003, filed Apr. 16, 2009, the subject matter of which is incorporated herein by reference in its entirety.

GOVERNMENT FUNDING

This invention was made with government support under Grant Nos. B3463R awarded by the Veterans Administration and PR043074 awarded by The Department of Defense under contract No. W81XWH-05-1-0389. The United States government has certain rights in the invention.

TECHNICAL FIELD

The present invention relates to joint bracing devices and, in particular, relates to an orthotic brace that provides variable resistance to movement between two bracing device portions.

BACKGROUND OF THE INVENTION

Orthotic bracing systems generally lock or otherwise constrain joints. An orthosis may constrain any range of motion in an ankle, knee, hip, or other joint. A thoracic jacket typically inhibits motion in the torso. An orthosis or brace for a joint may be unlocked during periods of rest for the wearer, but an orthosis or brace for a body segment such as the torso generally remain fully locked while the individual wears the brace. Therefore, there is value in a torso bracing mechanism that would allow freedom of movement of the torso during periods of rest while varying the amount of resistance to movement of the torso depending on the activity of the individual donning the brace.

Ankle-foot orthotic braces (AFOs) are commonly used in the treatment of disorders that affect muscle function, such as stroke, spinal cord injury, muscular dystrophy, cerebral palsy, polio, and multiple sclerosis. AFOs can also be used to provide support to weak or wasted limbs. An AFO is externally applied, and is intended to manage the position and velocity of the ankle joint, compensate for weakness, and/or correct deformities. AFOs are also used to immobilize the ankle and lower leg in the presence of arthritis or fracture, and to correct foot slap and foot drag.

An AFO is not designed to provide power to move the ankle by itself. Rather, it is an assistive device that is intended mainly as a controller of the ankle joint angle throughout the gait cycle. Some AFOs assist with toe-off, essentially the last movement in the gait cycle on one side that propels an individual forward to take another step. By assisting the subject with toe-off, the AFO helps delay muscle fatigue due to this high intensity work. Some AFOs help to prevent foot-drop, which is an inability to fully dorsi-flex, and presents itself in two forms during gait, namely, toe-drag and foot-slap. Toe-drag happens when the toe is dragged on the floor during the swing phase of gait, which is problematic because the subject is more susceptible to tripping. To counteract toe-drag, the subject's gait has to be altered to raise the ankle higher in all gait situations. The other symptom, foot-slap, occurs after heel strike in the gait cycle, when the muscles cannot impede the torque about the ankle and the foot literally and uncontrollably slaps the floor, which can injure the subject after repeated cycles.

One example of an AFO uses artificial pneumatic muscles because of their ability to mimic, both in control and power output, real muscles. One weakness of artificial muscles, however, is their power source, i.e., compressed air. To develop the torque needed for an AFO, the air compressor and other necessary components must be bulky and heavy. Another weakness is the pull-only actuation style, requiring either opposed pairs of pneumatic cylinders to produce both plantar and dorsi flexion or an opposing spring element to produce dorsi flexion.

Although AFOs exist that either assist or control dorsi flexion or plantar flexion, there is a need for an apparatus capable of providing both dorsi flexion and plantar flexion assistance. Accordingly, there is a need for an orthotic device for joint that provides variable resistance to movement of the joint.

SUMMARY OF THE INVENTION

In an aspect of the present invention, an orthotic brace for a joint includes a bracing device having first and second portions movable relative to one another and a mechanism for placing the bracing device in a first condition in which the first portion has a first resistance to movement relative to the second portion and a second condition in which the first portion has a second, different resistance to movement relative to the second portion. The mechanism is capable of placing the bracing device in a third condition in which the first portion has a third resistance to movement relative to the second portion that is between the first and second resistance.

In one aspect of the present invention, the first portion of the bracing device is secured to a first member of the joint and the second portion of the bracing device is secured to a second member of the joint. The first member of the joint may be a foot and the second member of the joint may be a leg.

In accordance with another aspect of the present invention, an orthotic brace for a joint includes a bracing device that has first and second portions movable relative to one another and a mechanism for placing the bracing device in a first condition in which the first portion has a first resistance to movement relative to the second portion and a second condition in which the first portion has a second, different resistance to movement relative to the second portion. The mechanism is capable of placing the bracing device in a third condition in which the first portion has a third resistance to movement relative to the second portion that is between the first and second resistance. The mechanism includes first and second brackets integral with the first and second portions of the bracing device. A plurality of force transmission elements are positioned between the first and second brackets. A cable extends through the force transmission elements and is secured to one of the first and second brackets. An actuator is connected to the cable for adjusting the distance between the first and second brackets to vary the compressive force upon the force transmission elements in order to place the bracing device in at least one of the first, second, and third conditions.

In accordance with another aspect of the present invention, an orthotic brace for a joint includes a bracing device that has first and second portions movable relative to one another and a linkage system for placing the bracing device in a first condition in which the first portion has a first resistance to movement relative to the second portion and a second condition in which the first portion has a second, different resistance to movement relative to the second portion. The linkage system is capable of placing the bracing device in a third condition in which the first portion has a third resistance to movement relative to the second portion that is between the first and second resistance. The linkage system includes a drive link pivotally connected to the second portion of the bracing device and a driven link rigidly connected to the first portion of the bracing device and pivotally connected to the second portion of the bracing device. A transmission link is pivotally connected to the drive link and the driven link. An elastic member is connected to the linkage system. The elastic member has a first position in which the drive link does not impart a moment to the driven link and a second position in which the drive link imparts a moment to the driven link. The first position of the elastic member places the bracing device in the first condition and the second position of the elastic member places the bracing device in the second condition.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 3A is a side view of a portion of the orthotic brace of FIG. 1 in a fully locked condition.

FIG. 3B is a side view of a portion of the orthotic brace in accordance with another aspect of the present invention.

FIG. 4A is a front view of a force transmission element in accordance with an aspect of the present invention.

FIG. 4B is a front view of another force transmission element in accordance with an aspect of the present invention.

DETAILED DESCRIPTION OF THE INVENTION

The present invention relates to joint bracing devices and, in particular, relates to an orthotic brace that provides variable resistance to movement between two bracing device portions. Varying the resistance to movement between portions of the bracing device varies the rigidity of the bracing device. The orthotic brace of the present invention may be used to constrain or assist any range of motion in any joint in the body, e.g., ankle, knee, hip, elbow, shoulder, wrist, or vertebral joint.

Figure 1:
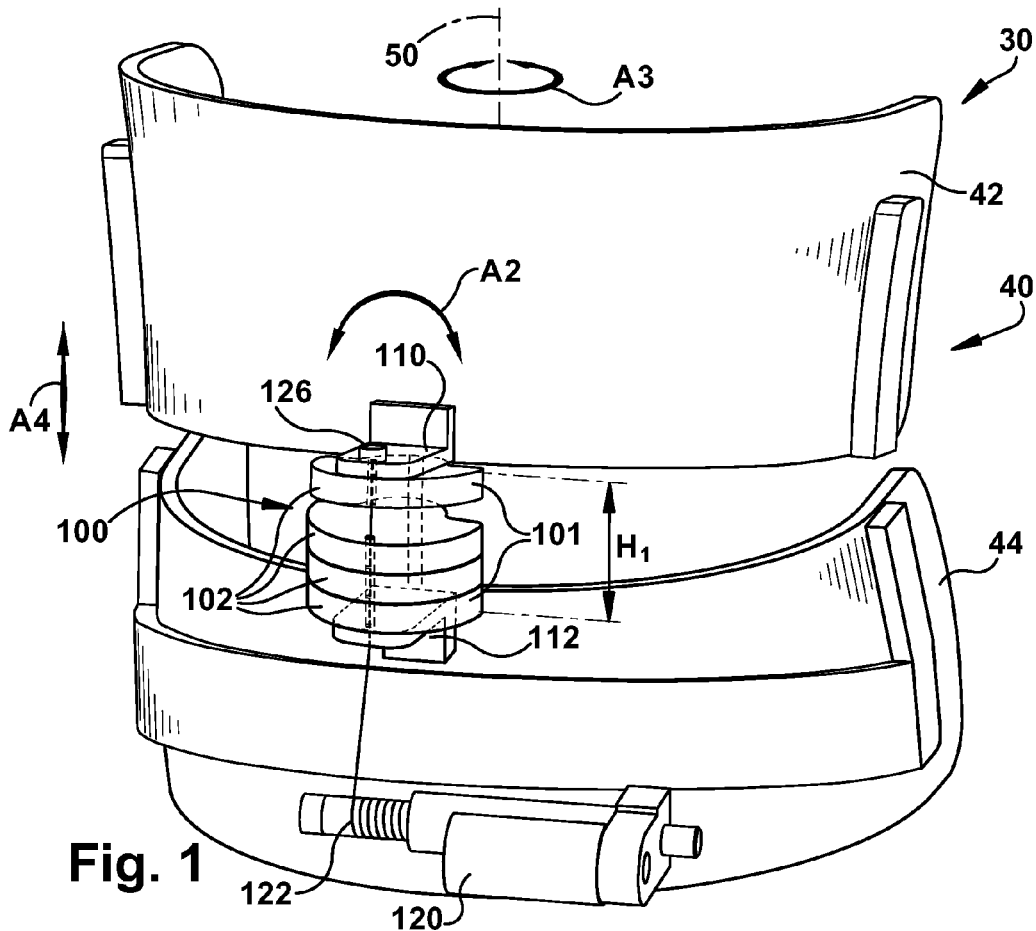
FIG. 1 is a schematic illustration of an orthotic brace in accordance with the present invention.
Figure 2:
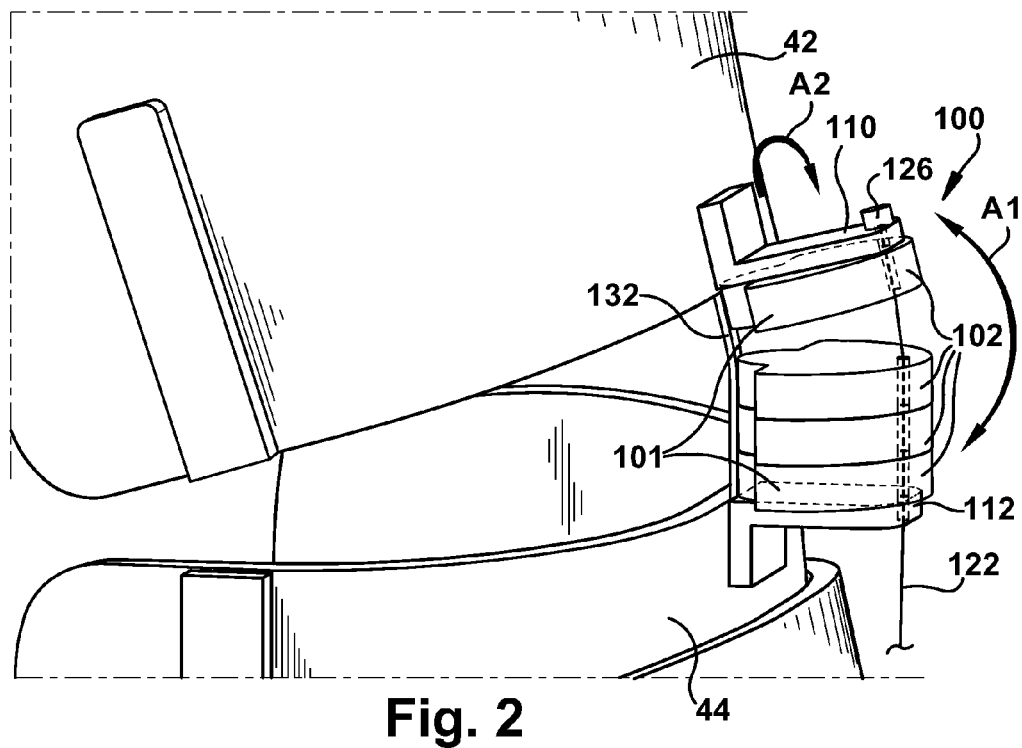
FIG. 2 is a side view of the orthotic brace of FIG. 1.

One example of orthotic brace 30 in accordance with the present invention is illustrated in FIGS. 1-2. The orthotic brace 30 includes a bracing device 40 having a first portion 42 and a second portion 44, which are movable relative to one another. The first portion 42 and the second portion 44 may be substantially centered about a longitudinal axis 50 about which the first portion and/or the second portion move. In use, the first portion 42 is secured to a wearer on one side of a joint for which motion is to be constrained or assisted, and the second portion 44 is secured to the wearer on the opposite side of the joint.

The first and second portions 42, 44 of the bracing device 40 may, for example, constitute upper and lower portions of a trunk corset configured to be worn by a human being. An individual may wear a trunk corset to brace the back following injury, surgery or in situations where the back has reduced mobility or flexibility due to illness, chronic disease, or other causes. For example, the bracing device 40 may be worn for the treatment of scoliosis.

As shown in FIGS. 1 and 2, the first and second portions 42, 44 are particularly configured for use as upper and lower portions of a trunk corset. Each of the first and second portions 42, 44 is generally C-shaped with the ends of the C-shape to be positioned adjacent the wearer's sides and the center portion of the C-shape to be positioned across the wearer's back. The first and second portions 42, 44 are formed of rigid or semi-rigid material, such as metal or stiff plastic, to provide necessary support to the wearer. To secure the first and second portions 42, 44 to the wearer, each end of the C-shape of each portion may be attached to one or more bands (not shown) of flexible material, such as fabric or flexible plastic. The bands attached to the ends of the C-shape of each of the first and second portions 42, 44 may be releasably joined to one another by, for example, buckles or hook-and-loop fasteners (not shown) positioned at the front of the wearer. Each of the first and second portions 42, 44 and its associated bands may thus encircle the torso of the wearer with the associated releasable fasteners positioned to facilitate donning and doffing the bracing device 40.

The first and second portions 42, 44 are connected to one another by a mechanism 100 that controls the resistance to movement of the first and second portions relative to one another in at least one degree of freedom. For example, the mechanism 100 may control resistance to movement between the first and second portions 42, 44 of the bracing device 40 in four degrees of freedom. Where the bracing device 40 is a trunk corset, each degree of freedom of movement corresponds with a motion of the torso of the wearer of the bracing device, namely, front/rear bending, side bending, rotation about the hips, and extension/contraction. These degrees of freedom of movement are represented by arrows $A_1$-$A_4$, respectively, in FIGS. 1-2.

The mechanism 100 includes a plurality of force transmission elements 102 that are arranged in a column or stack. The column of force transmission elements 102 extends generally parallel to the axis 50 of the bracing device 40. As shown in FIGS. 3A-B, the force transmission elements 102 comprise a column of axially aligned plates. Although four plates 102 are illustrated, those having ordinary skill will appreciate that more or fewer plates may be used in accordance with the present invention. The force transmission elements 102 are positioned between first and second brackets 110, 112, which are integral with (either formed in one piece with or formed separately and secured to) the first portion 42 and the second portion 44, respectively, of the bracing device 40. The outermost plate 101 at each end of the column is rigidly secured to one of the brackets 110, 112 such that movement of the bracket results in movement of the plate secured to the bracket. The plates 102 in the column between the outermost plates 101 are movable relative to one another and the brackets 110, 112. Alternatively, no plates may be secured directly to the brackets 110, 112.

A wire or cable 122 extends through openings in the brackets 110, 112 and openings in the plates 101, 102 and maintains the plates in a stacked configuration between the brackets. A stop 126 is secured to an end of the cable 122 to prevent the cable from being drawn out of or otherwise exiting the openings in the brackets 110, 112 or the openings in the plates 101, 102. The stop 126 is positioned adjacent to, and may be secured to, either the first bracket 110 or the second bracket 112.

As shown in FIG. 1, the stop 126 is positioned atop and secured to the bracket 110 on the first portion 42 of the bracing device 40. The cable 122 extends downward through the bracket 110, the plates 101, 102, and the bracket 112 on the second portion 44 of the bracing device 40. The cable 122 may constitute a flexible cable made of metal or similarly durable material. The cable 122 is connected to an actuator 120 for controlling the tension of the cable. The actuator 120 includes an electric motor with a rotating output shaft to wind and unwind the cable 122 about the shaft. Alternatively, the actuator 120 may constitute a linear actuator or other actuator or device capable of controlling the tension in the cable 122. The actuator 120 is connected to a power source, such as a battery (not shown).

The actuator 120 is connected to the second portion 44 of the bracing device 40. The power source (not shown) may also be mounted on the second portion 44. Mounting the actuator 120 and the power source on the second portion 44 helps to keep the weight and center of gravity of the bracing device 40 lower on the wearer's body. Alternatively, the actuator 120 may be connected to the first portion 42 of the bracing device 40 and the cable 122 may extend through the brackets 110, 112 and the plates 101, 102, terminating at the end stop 126 secured to the bracket 112. In any case, the application of tension to the cable 122 by the actuator 120, e.g., winding, causes the brackets 110, 112 to move closer to one another while the reduction of tension, e.g., unwinding, allows the brackets to move farther from one another.

Since the cable 122 is fixed to the first bracket 110 via the stop 126 while being freely slidable through the second bracket 112, any tension applied to the cable will urge the first bracket downwards and towards the second bracket and, thus, move the first and second portions 42, 44 of the bracing device 40 closer to one another. As shown in FIG. 3, actuation of the actuator 120 increases tension in the cable 122 in the direction indicated by F to move the first bracket 110 downward and closer to the second bracket 112.

In an initial, fully unlocked condition of the bracing device 40, the cable 122 has little or no tension, and the brackets 110, 112 are spaced apart by a predetermined first distance indicated by $H_1$. The first bracket 110 and the plate 101 secured to the first bracket are spaced from the plates 102. Thus, the brackets 110, 112 do not apply a compressive force to the column of plates 101, 102 when the brackets are spaced apart by at least the predetermined distance $H_1$. In this condition, the plates 102 are able to move relative to one another and the plates 101 when the portions 42, 44 of the bracing device 40 move in response to user activity. Therefore, the plates 102 do not prohibit or substantially hinder movement of the portions 42, 44 of the bracing device 40 caused by movement of the user's torso in any of the degrees of freedom $A_1$-$A_4$. The fully unlocked condition of the bracing device 40 thereby provides substantially no resistance to movement of the bracing device 40 to allow the user, for example, to sit, rest, freely reach for objects or maneuver a wheelchair without experiencing resistance from the bracing device.

It will be recognized that the phrase "substantially no resistance to movement" contemplates the possibility of some minimal restriction on motion due to the construction of the mechanism 100. For example, during extreme side bending by the wearer of the bracing device 40, the movements of the plates 102 relative to one another may be constrained by the presence of the cable 122, which may limit lateral movement or tipping movement of the plates relative to one another in order to maintain the integrity of the mechanism 100.

By adjusting the distance between the brackets 110, 112 on the portions 42, 44 of the bracing device 40, the frictional forces between the plates 101, 102 can be adjusted to vary the resistance to movement of the bracing portions. As the distance between the brackets 110, 112 decreases below $H_1$, the space between the plate 101 secured to the first bracket 110 and the plates 102 decreases until the plate on the first bracket engages the adjacent plate 102, causing both brackets to apply a compressive force to the plates as indicated at arrows C in FIG. 3A. As the brackets 110, 112 continue moving closer together, the ability of the plates 102 to move relative to one another decreases because the increase in compressive force C applied by the brackets 110, 112 increases the frictional forces between adjacent plates.

As the frictional forces between plates 101, 102 increases, the resistance to movement between the first and second portions 42, 44 of the bracing device 40 likewise increases until the plates 101, 102 become locked as a single, rigid column between the brackets 110, 112. In this fully locked condition, the brackets 110, 112 are spaced apart by a distance $H_2$ less than the distance $H_1$, and the plates 101, 102 are substantially parallel to one another. The distance $H_2$ is the minimum distance by which the brackets 110, 112 can be spaced without plastically deforming or damaging the plates 101, 102.

Although the plates 101, 102 are illustrated in FIGS. 1-3A as being in direct contact with one another, a material 130, such as rubber or polyurethane, may be applied as a layer or as a thin film or coating secured to at least one surface of at least one of the plates in order to reduce the likelihood of slippage or rotation between the plates as tension in the cable 122 is increased (see FIG. 3B). For example, the material 130 may be an elastomer bonded to both adjacent surfaces of all adjacent plates 101, 102, which may constrain lateral and rotational movement of the plates relative to one another and constrain the vertical spacing between the plates. By placing the material 130 between the plates 102, the compressive force C applied by the brackets 110, 112 may be more evenly distributed across the plates to ensure that the plates remain substantially parallel to one another when tension in the cable 122 is increased. As an alternative to a layer, film or coating of material 130, the surfaces of the plates 101, 102 may be mechanically or chemically roughened (not shown) to inhibit lateral and rotational movement of the plates relative to one another. The parallel alignment of the plates 102 in the column also reduces the likelihood of slippage or rotation between the plates as the brackets 110, 112 are drawn closer together and thereby helps to lock the plates together more securely.

Alternatively or additionally, a force restoring element 132 may be provided to bias the plates 102 into vertical alignment with one another such that the cable 122 extends substantially unimpeded through the plates in the column. The force restoring element 132 may be made of an elastomer or other suitable material capable of biasing the column of plates 101, 102 into a predetermined configuration. In other words, the force restoring element 132 may resist movement of the plates 102 in the plane perpendicular to the axis 50 of the bracing device 40. The force restoring element 132 may be secured to a portion of each plate 102 at, for example, the periphery of each plate (FIG. 3) or may extend through openings in the plates.

In use, when it is desirable to allow for free movement of the first and second portions 42, 44 of the bracing device 40, e.g., when the user is at rest, the actuator 120 can unwind the cable 122 sufficiently to allow the brackets 110, 112 to be spaced apart by at least the distance $H_1$ to place the bracing device in the fully unlocked condition and enable resistance-free movement of the bracing device. More specifically, the unwound cable 122 applies relatively little force upon the stop 126 and, thus, the first bracket 110 is not urged towards the second bracket 112. Therefore, the brackets 110, 112 do not apply a compressive force to the plates 101, 102 and, thus, movement of the portions 42, 44 of the bracing device 40 is not impeded, i.e., the bracing device is capable of substantially resistance-free movement.

If it is desirable to lock the bracing device 40 completely and thereby prevent any relative movement between the first and second portions 42, 44, e.g., during designated activity by the user, the actuator 120 may wind up the cable 122 to draw the brackets 110, 112 closer together than the distance $H_1$. As the distance between brackets 110, 112 decreases, the plate 101 secured to the first bracket engages the adjacent plate 102 and the brackets cooperate to apply compressive force C to the column of plates 101, 102, causing frictional forces between adjacent plates to increase. When the spacing between the brackets 110, 112 eventually reaches the predetermined distance $H_2$, the plates 101, 102 and brackets become locked together in a rigid column. Locking the plates 101, 102 and brackets 110, 112 together prevents relative movement between the first and second portions 42, 44 of the bracing device 40 and, thus, places the bracing device in the fully locked condition. In other words, the first and second portions 42, 44 of the bracing device 40 are prevented from moving in any of the degrees of freedom $A_1$-$A_4$ due to the high frictional resistance between the plates 101, 102.

Since the actuator 120 controls the degree of winding or unwinding of the cable 122 and, thus, the level of tension in the cable, the mechanism 100 of the present invention is able to control with substantial precision the amount of frictional forces between the plates 101, 102. Not only can the actuator 120 unwind the cable 122 sufficiently to unlock the bracing device 40 completely, i.e., to permit substantially resistance-free movement, or wind the cable sufficiently to lock the bracing device completely, i.e., to provide maximum resistance to movement, the actuator may place the bracing device in any condition between the fully locked condition and the fully unlocked condition by adjusting the tensioning force in the cable. In other words, the actuator 120 may cause the brackets 110, 112 to be spaced apart by the first distance $H_1$ corresponding with the fully unlocked condition, the second distance $H_2$ corresponding with the fully locked condition, or any distance in between $H_1$ and $H_2$ corresponding with a condition between the fully unlocked and fully locked conditions. The actuator 120 may be equipped with limit switches or an encoder (not shown) for monitoring the tension in the cable 122 in order accurately to provide any desirable resistance to movement between the first and second portions 42, 44 of the bracing device 40.

The bracing device 40 may also be provided with a microprocessor and/or memory device (not shown) for storing preset or learned tension settings to allow the wearer accurately and quickly adjust the resistance to movement between the first and second portions 42, 44. Such a microprocessor and/or memory device may be mounted on either the first portion 42 or the second portion 44 of the bracing device or mounted or carried separately by the wearer with a wired or wireless connection to the actuator 120.

When the brackets 110, 112 are spaced apart a distance between the first distance $H_1$ and the second distance $H_2$, the brackets supply a compressive force C to the plates 101, 102 that hinders but does not prevent relative movement between the plates 101, 102. In other words, the compressive force C is sufficient to increase frictional forces between the plates 101, 102 but these frictional forces may be overcome by the user providing sufficient force to the portions 42, 44 of the bracing device.

Although resistance to movement between the portions 42, 44 of the bracing device of FIGS. 1-3 is provided by varying the frictional forces between force transmission elements, those having ordinary skill will understand that alternative mechanisms using other types of loading may be employed to supply variable resistance to movement between portions of the bracing device, e.g., spring force in compression or tension, dynamic friction, moments, torques, etc.

Figure 4B:
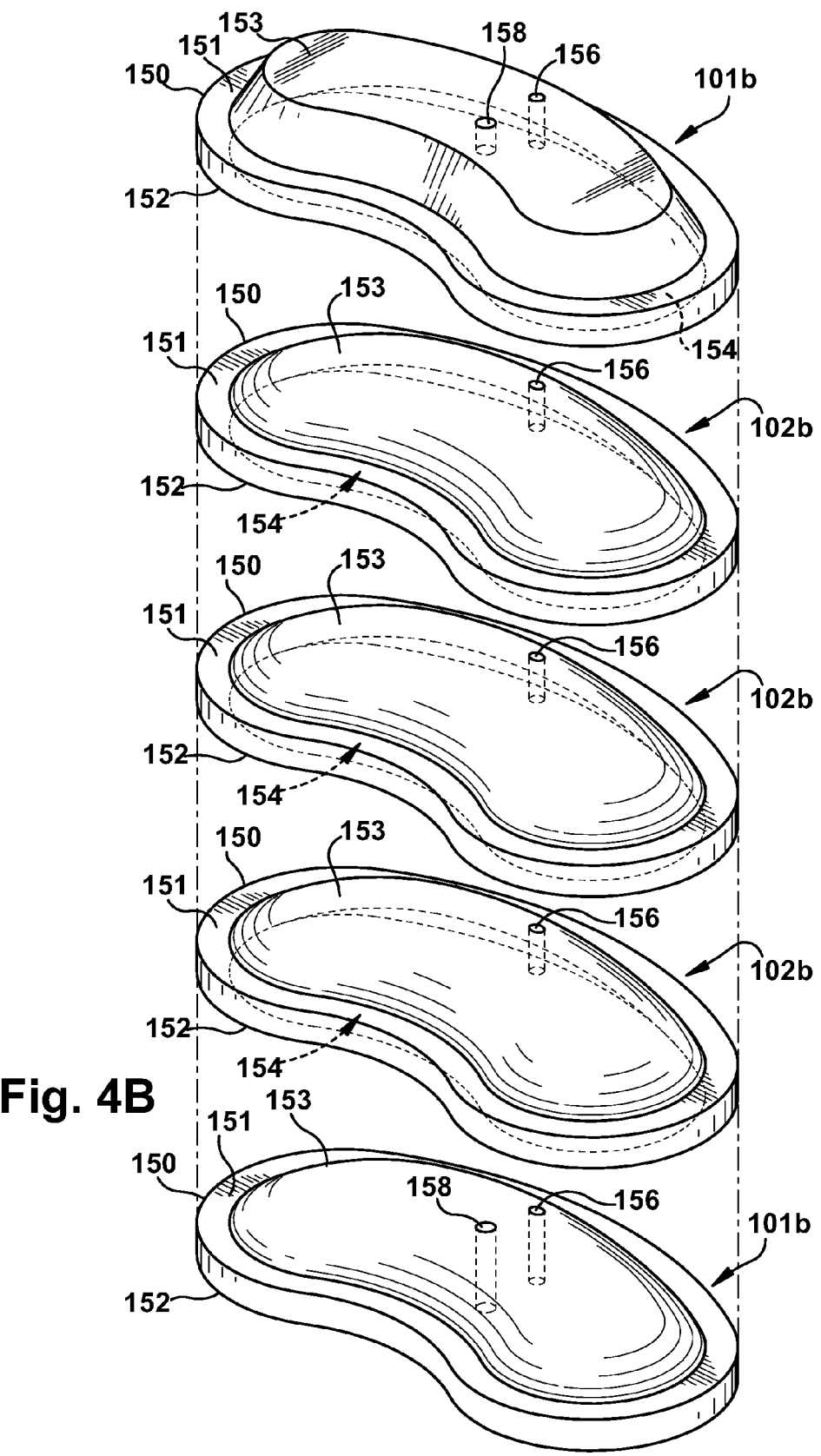
FIG. 4B is a schematic illustration of an alternative force transmission element in accordance with an aspect of the present invention.

Alternative examples of force transmission elements in accordance with the present invention are illustrated in FIGS. 4A-4F. In FIG. 4A, the force transmission elements 102a constitute hollow plates. Each plate 102a includes a base 140 having a first member 142 and second member 144 spaced from and interconnected to the first member to form a substantially oval base. Openings 146 in one end of the base 140 extend through the first and second members 142, 144. The openings 146 are axially aligned with one another and are configured to receive the cable 122 attached to the actuator 120. A pair of aligned openings 147 at the opposing end of the plate 102a may be used to secure the plate to the first bracket 110 or the second bracket 112.

The base 140 further includes a pair of openings 148 positioned near the center of the base that extend through the first and second members 142, 144. The openings 148 are configured to receive the force damping member 130 for biasing the plates 102a into vertical alignment with one another during locking and unlocking of the bracing device 40. The aligned plates 102a allow the cable 122 to pass cleanly through the column without kinking or deviating from a substantially straight path.

Alternatively, two of the openings 146, 147, 148 each receive a cable 122 and the remaining opening helps to secure the plates 101 to the first bracket 110 and the second bracket 112. In this configuration, both cables 122 are used to lock and unlock the bracing device 40. The use of two cables 122 also eliminates the need for a force damping member 130.

Similar to the plates 102 of FIGS. 1-3, a plurality of plates 102a are positioned between the brackets 110, 112 with the outermost plate being rigidly secured to each brackets. Alternatively, none of the plates 102a may be secured to the brackets 110, 112. The cable 122 extends through the openings 146 in the plates 102a and is attached to the actuator 120 for adjusting the distance between the brackets 110, 112 in order to adjust the frictional forces between adjacent plates and thereby adjust the resistance to movement of the bracing device portions 42, 44 relative to one another along a continuum from a fully unlocked, i.e., resistance-free, condition to a fully locked, i.e., maximum resistance, condition.

In FIG. 4B, the force transmission elements 102b constitute a series of nesting elements. Each nesting element 102b has a kidney bean shape and includes a base 150 that has a top surface 151 and a bottom surface 152. A protrusion 153 extends from the top surface 151 of the base 150 and is offset from the periphery of the base. On the nesting element 101b secured to the bracket 110, the protrusion 153 has a generally frustoconical configuration in order to sit flush against the underside of the bracket, while the protrusions on the remaining nesting plates have the same domed shape. A recess 154 is formed in each nesting element 102b except the nesting element 101b secured to the bottom bracket 112 such that the nesting element sits flush against the bracket. The recess 154 extends from the bottom surface 152 of the base 150 into the protrusion 153. The recess 154 has a domed shape and is offset from the periphery of the base 150 such that the protrusion 153 and recess extend parallel to one another.

A first opening 156 extends through the protrusion 153 and the base 150 of each nesting element 102b for receiving the cable 122 attached to the actuator 120. A second opening 158 extends through the protrusion 153 and the base 150 of the nesting elements 101b for securing the nesting element 102b to the first bracket 110 and the second bracket 112.

The elements 102b are configured to nest within one another when positioned between the brackets 110, 112 on the bracing device 40. In particular, the nesting elements 102b are configured such that the protrusion 153 of one nesting element is positioned within the recess 154 of an adjacent nesting element to form a compact stack. Since the protrusion 153 and recess 154 of each nesting element 120b is spaced from the periphery of the base 150, the base of each nesting element sits flush with the base of the adjacent nesting element when the protrusions nest within the recesses, adding stability to the nesting element stack.

In use, the cable 122 extends through the openings 156 in the nesting elements 102c and is attached to the actuator 120 for adjusting the distance between the brackets 110, 112 in order to adjust the frictional forces between adjacent nesting elements and thereby adjust the resistance to movement between portions 42, 44 of the bracing device 40 along a continuum from a fully unlocked condition to a fully locked condition.

Figure 4C:
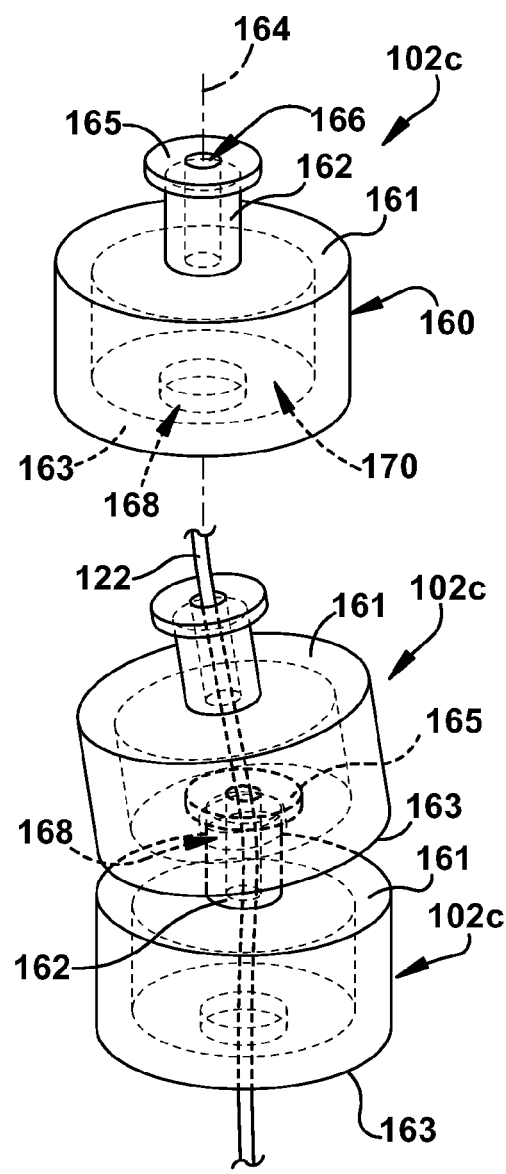
FIG. 4C is a front view of another force transmission element in accordance with an aspect of the present invention.

In FIG. 4C, the force transmission elements 102c constitute a series of interlocking elements. Each interlocking element 102c has a generally cylindrical shape and includes a base 160 and an extension 162 that extends axially from the base. The base 160 and the extension 162 extend generally along an axis 164. The base 160 includes a top surface 161 and a bottom surface 163 spaced from the top surface. The extension 162 extends from the top surface 161 of the base 160 and includes a passage 166 for receiving the cable 122 attached to the actuator 120. The extension 162 terminates at an enlarged portion 165 made of a flexible but resilient material.

The base 160 includes an opening 168 that leads into a passage 170 within the base. The cable 122 extends through the passage 166 in the extension 162, the passage 170 in the base 160, and out of the interlocking element 102c via the opening 168. The opening 168 in the base 160 of one interlocking element 102b is configured to receive the enlarged portion 165 of an adjacent interlocking element. The enlarged portion 165 of the extension 162 is sized and configured to be pushed through the opening 168 of the base 160 and into the passage 170 but not easily removed. In particular, the enlarged portion 165 has a larger cross-section than the diameter of the opening 168 in the base 160 but may be made of a flexible material that allows the enlarged portion to deform and be forced through the opening in the base.

Once the enlarged portion 165 reaches the passage 170 in the base 160, it may flexibly return to its initial configuration and thereby inhibit removal of the enlarged portion from the base. The enlarged portions 165 of each interlocking element 102c thus cooperate with the openings 168 in adjacent interlocking elements to connect the elements with one another such that any number of interlocking elements can be interconnected in a continuous chain.

Each extension 162 is sized to be smaller than the opening 168 in the base 160 to allow the extension of one interlocking element 102c to move relative to the base of an adjacent, interlocked element. Moreover, the passage 170 in the base 160 is large enough to accommodate movement of the enlarged portion 165 of the extension 162. This relative movement allows adjacent interlocking elements 102c to tilt or rotate relative to one another without plastically deforming in order to adjust to bending of the bracing device 40 caused by movement of the bracing portions 42, 44 in one or more degrees of freedom $A_1$-$A_3$ so long as the bracing device 40 is not in the fully locked condition.

In the fully unlocked condition, the interlocking elements 102c are free to move relative to one another under the influence of movement of the bracing device 40. In particular, the bottom surfaces 163 of the bases 160 rest atop the top surfaces 161 of adjacent bases in the column of interlocking elements 102c. At least one of the brackets 110, 112, however, is spaced relative to the elements 102c such that no compressive force C is applied to the stack of interlocking elements. Therefore, the interlocking elements 102c are free to move relative to one another during movement of the portions 42, 44 of the bracing device 40.

The cable 122 extends through the openings 166, 168 in the interlocking elements 102c and is attached to the actuator 120 for adjusting the distance between the brackets 110, 112 in order to adjust the frictional forces between adjacent interlocking elements and thereby adjust the resistance to movement between portions 42, 44 of the bracing device 40 along a continuum from a fully unlocked condition to a fully locked condition. Since the interlocking elements 102c remain connected regardless of the condition of the bracing device 40, the cable 122 extending through the openings 166, 168 may experience reduced friction, thereby improving performance when it is desirable to have low rigidity, i.e., high mobility, in the bracing device 40.

Figure 4D:
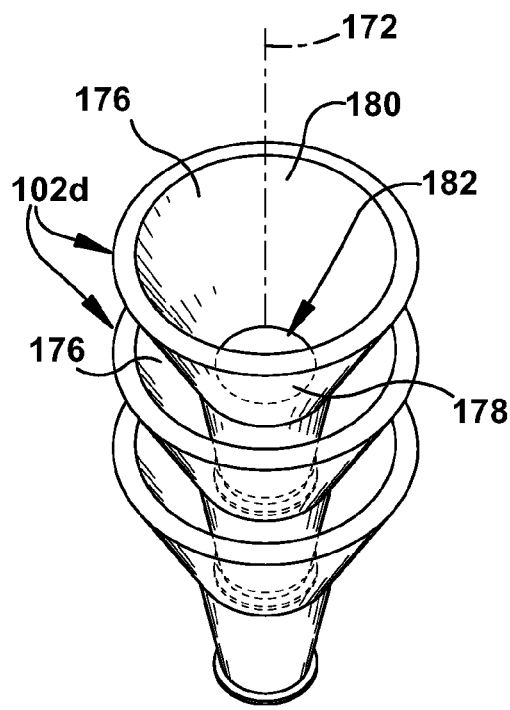
FIG. 4D is a front view of another force transmission element in accordance with an aspect of the present invention.
Figure 4E:
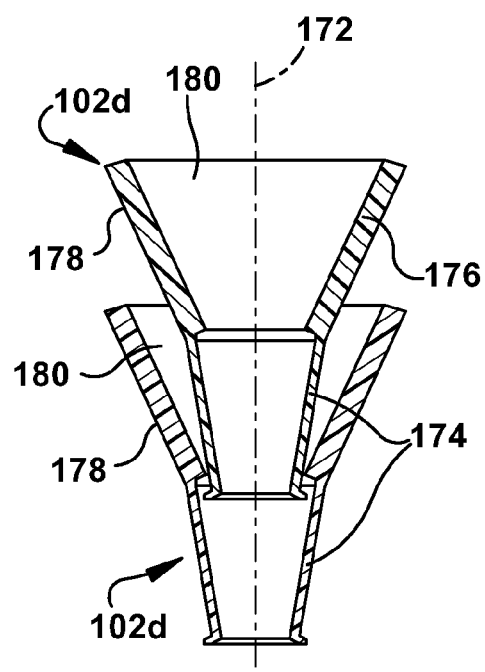
FIG. 4E is a sectional view of the force transmission element of FIG. 4D.

In FIGS. 4D-E, the force transmission elements 102d constitute a series of nesting elements. Each nesting element 102d extends along an axis 172 and includes a base 174 and a receiving portion 176 extending axially from the base. Although the base 174 and receiving portion 176 are illustrated as having a frustoconical shape, the base and receiving portion may have any suitable shape. Each nesting element 102d includes an outer surface 178 and a substantially concentric inner surface 180. The inner surface 180 defines a passage 182 that extends entirely through the nesting element 102d. The passage 182 is configured to receive the cable 122 secured to the actuator 120.

The nesting elements 102d nest with one another when positioned between the brackets 110, 112 on the bracing device 40. In particular, the nesting elements 102d are configured such that the base 174 of one nesting element extends through the receiving portion 176 of an adjacent nesting element and into the base of the adjacent receiving portion. This places the receiving portion 176 of one nesting element 102d into engagement with the receiving portion of the adjacent nesting element. Due to this configuration, the nesting elements 102d are capable of tilting relative to one another to allow the column of nesting elements to bend during movement of the bracing portions 42, 44 so long as the bracing device 40 is not in the fully locked condition. More specifically, the narrower base 174 of each nesting element 102d is capable of tilting within the wider receiving portion 176 of the adjacent element along the inner surface 180.

The cable 122 extends through the passages 182 in the nesting elements 102d and is attached to the actuator 120 for adjusting the distance between the brackets 110, 112 in order to adjust the frictional forces between adjacent nesting elements and thereby adjust the resistance to movement between portions 42, 44 of the bracing device 40 along a continuum from a fully unlocked condition to a fully locked condition.

Figure 4F:
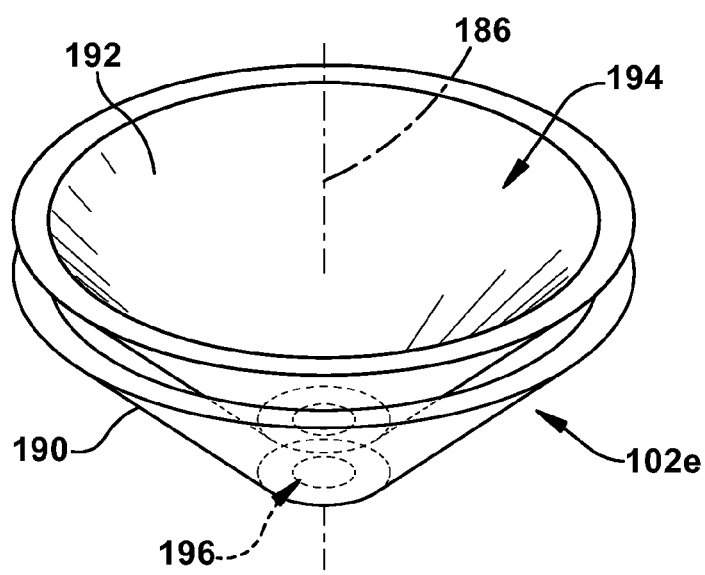
FIG. 4F is a front view of another force transmission element in accordance with the present invention.

In FIG. 4F, the force transmission elements 102e constitute a series of mating elements. Each mating element 102e extends along an axis 186 and includes an outer surface 190 and a substantially concentric inner surface 192. The inner surface 192 defines a receiving portion 194 that leads to an opening 196 extending entirely through the mating element 102e. The cable 122 from the actuator 120 extends through the receiving portion 194 and the opening 196. Although the mating element 102e is illustrated as having a frustoconical shape, the mating element may have any suitable shape.

The mating elements 102e are configured such that the outer surface 190 of one mating element mates with the inner surface 192 of the adjacent mating element when the elements are positioned between the brackets 110, 112 on the bracing device 40. The surfaces of the mating elements 102e may be configured to resist relative rotation between adjacent mating elements. In particular, the outer surface 190 and/or the inner surface 192 may be lined with an elastomeric material, such as polyurethane. Alternatively, the outer surface 190 and/or inner surface 192 of the mating elements 102e may be mechanically or chemically roughened to resist relative rotation between adjacent mating elements.

In use, the cable 122 extends through the openings 196 in the mating elements 102e and is attached to the actuator 120 for adjusting the distance between the brackets 110, 112 in order to adjust the frictional forces between adjacent mating elements and thereby adjust the resistance to movement between portions 42, 44 of the bracing device 40 along a continuum from a fully unlocked condition to a fully locked condition.

Although the force transmission elements 102e illustrated in FIG. 4F may include structure for resisting relative rotation between adjacent force transmission elements, those having ordinary skill in the art will appreciate that any of the force transmission element configurations 102-102e may exhibit such structure, e.g., mechanical or chemical roughening or etching, the application of layers or films of elastomers or other materials between elements, etc., in accordance with the present invention.

Figure 5:
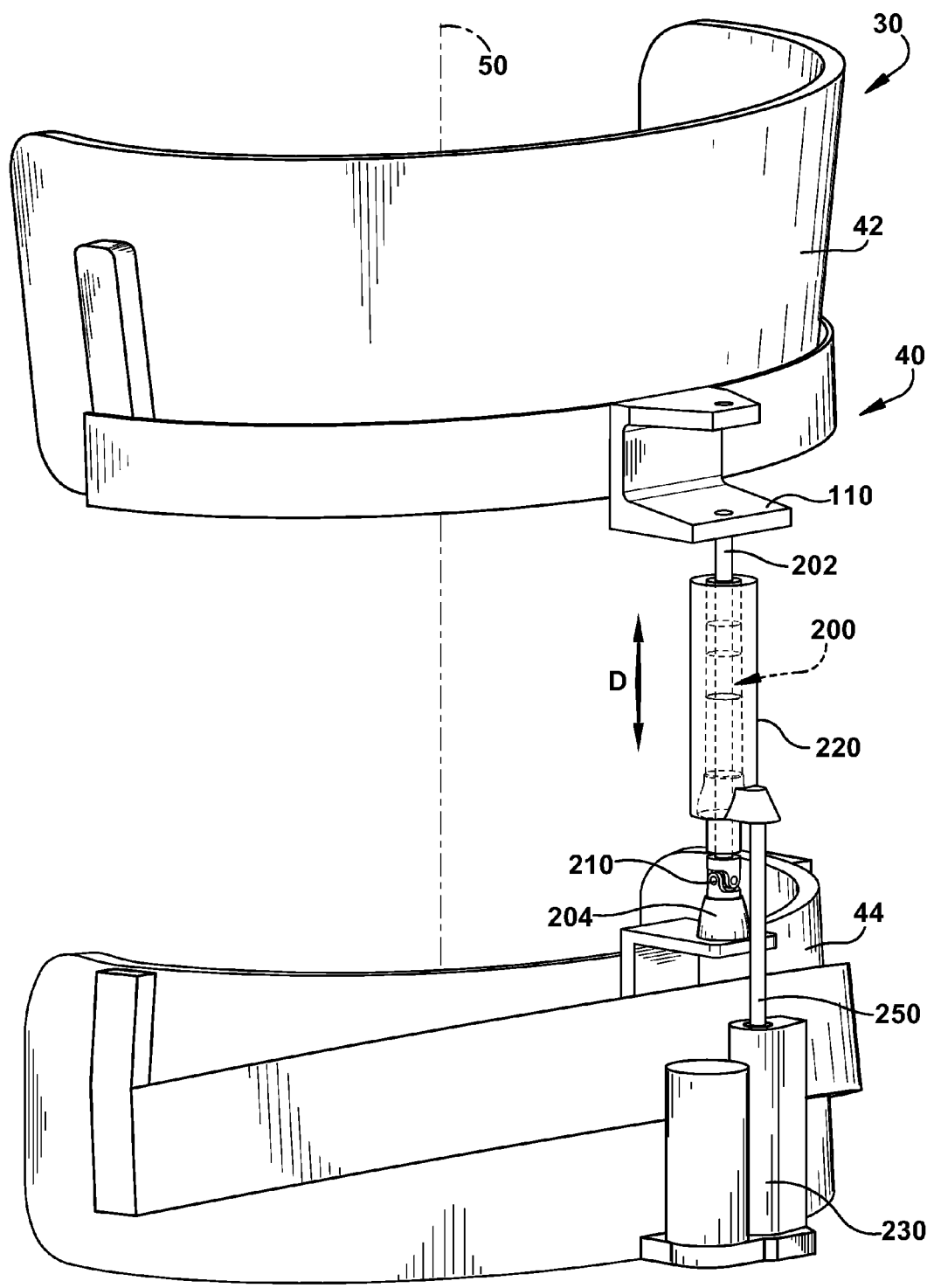
FIG. 5 is a schematic illustration of a resistance control mechanism for an orthotic brace in accordance with the present invention.
Figure 6A:
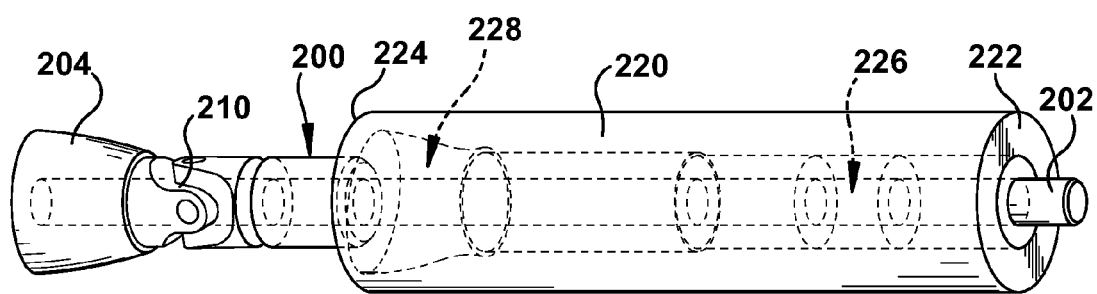
FIG. 6A is a side view of the resistance control mechanism of FIG. 5.
Figure 6B:
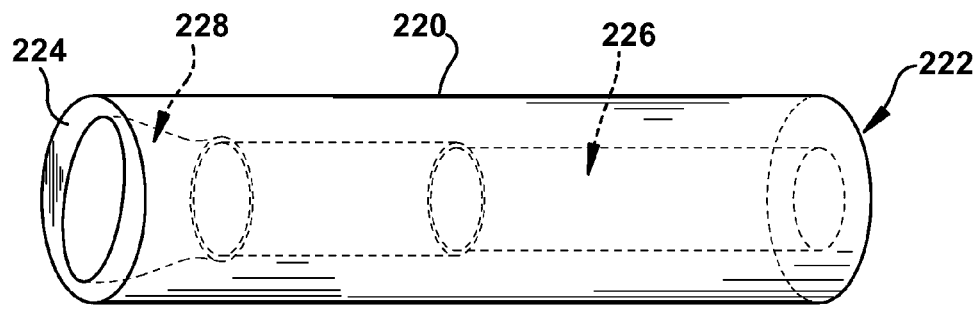
FIG. 6B is a side view of a sleeve of the resistance control mechanism of FIG. 5.

FIGS. 5-6B illustrate an alternative embodiment of the present invention in which a universal joint assembly 200 is secured between the first and second portions 42, 44 of the bracing device 40. Alternatively, a string of universal joint assemblies 200 is secured in series between the first and second portions 42, 44 of the bracing device 40. The universal joint assembly 200 includes a first portion 202 secured to the first bracket 110 and a second portion 204 secured to the second bracket 112. The first portion 202 and second portion 204 are movable relative to one another about a universal or cardan joint 210 that provides three degrees of freedom of movement between the portions 42, 44 of the bracing device 40.

A sleeve 220 is provided for sliding movement along and relative to the universal joint assembly 200. As shown in FIGS. 6A-B, the sleeve 220 has a cylindrical shape and extends from a first end 222 to a second end 224. A first passage 226 extends axially through the sleeve 220 from the first end 222 towards the second end 224. Throughout its length, the passage 226 has a circular shape configured for receiving the first portion 202 of the universal joint assembly 200. A second passage 228 extends from the first passage 226 to the second end 224 of the sleeve 220. The second passage 228 is tapered and is configured to receive the second portion 204 and the joint 210 of the universal joint assembly 200.

A linear actuator 230 is secured to the second portion 44 of the bracing device 40 and is connected to the sleeve 220 via a semi-rigid connecting member 250 to move the sleeve relative to the universal joint assembly in the direction indicated by arrow D in FIG. 5. The connecting member 250 must be rigid enough to transmit upward motion, as viewed in FIG. 5, of the actuator 230 to the sleeve 220, while also being flexible enough to permit the full range of desired motion of the universal joint 210. When the sleeve 220 is spaced entirely from the universal joint 210 of the universal joint assembly 200, the universal joint is capable of resistance-free movement and, thus, the bracing portions 42, 44 secured to the universal joint move substantially resistance free. When the sleeve 220 is moved downward by the actuator 230, the sleeve slides over the universal joint 210 and ultimately the second end 204 of the universal joint assembly 200. This causes the universal joint 210 and the second portion 204 to be received in the tapered passage 228 of the sleeve 220. The passages 226, 228 are sized such that the portions 202, 204 of the universal joint assembly 200 cannot move relative to one another when the sleeve 220 fully covers the second portion of the universal joint assembly. Accordingly, when the sleeve 220 overlies the second portion 204 of the universal joint assembly 200, the sleeve resists all movement of the universal joint assembly, thereby fully locking the universal joint assembly and, thus, the bracing device 40.

The actuator 230 is capable of moving and stopping the sleeve 220 relative to the universal joint assembly 200 such that any amount of the universal joint 210 and the second portion 204 of the universal joint assembly is received in the sleeve 220. Due to the configuration of the passage 226 and the tapered passage 228 in the sleeve 220, when the universal joint 210 and the second portion 204 of the universal joint assembly 200 are partially received in the sleeve, the sleeve will allow for partial movement of the portions 202, 204 of the universal joint assembly between no movement, i.e., the fully locked condition, and free movement, i.e., the fully unlocked condition. Accordingly, the sleeve 220 of the present invention may be placed in different positions relative to the universal joint assembly 200 to vary the resistance to movement of the portions 202, 204 of universal joint and, thus, of the bracing portions 42, 44 along a continuum from a fully unlocked condition to a fully locked condition.

Figure 7:
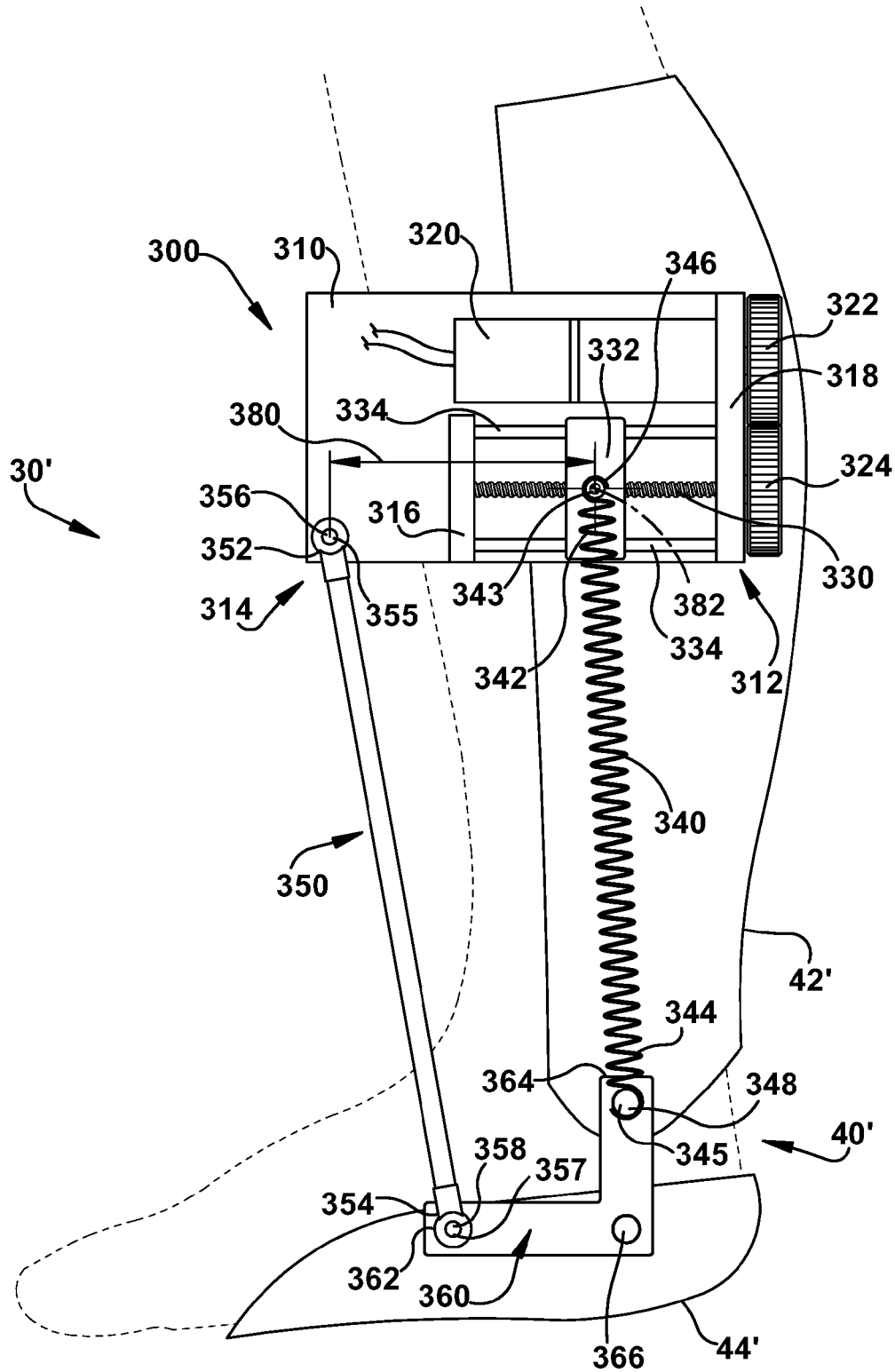
FIG. 7 is a schematic illustration of an orthotic brace for an ankle in a first condition accordance with the present invention.
Figure 8:
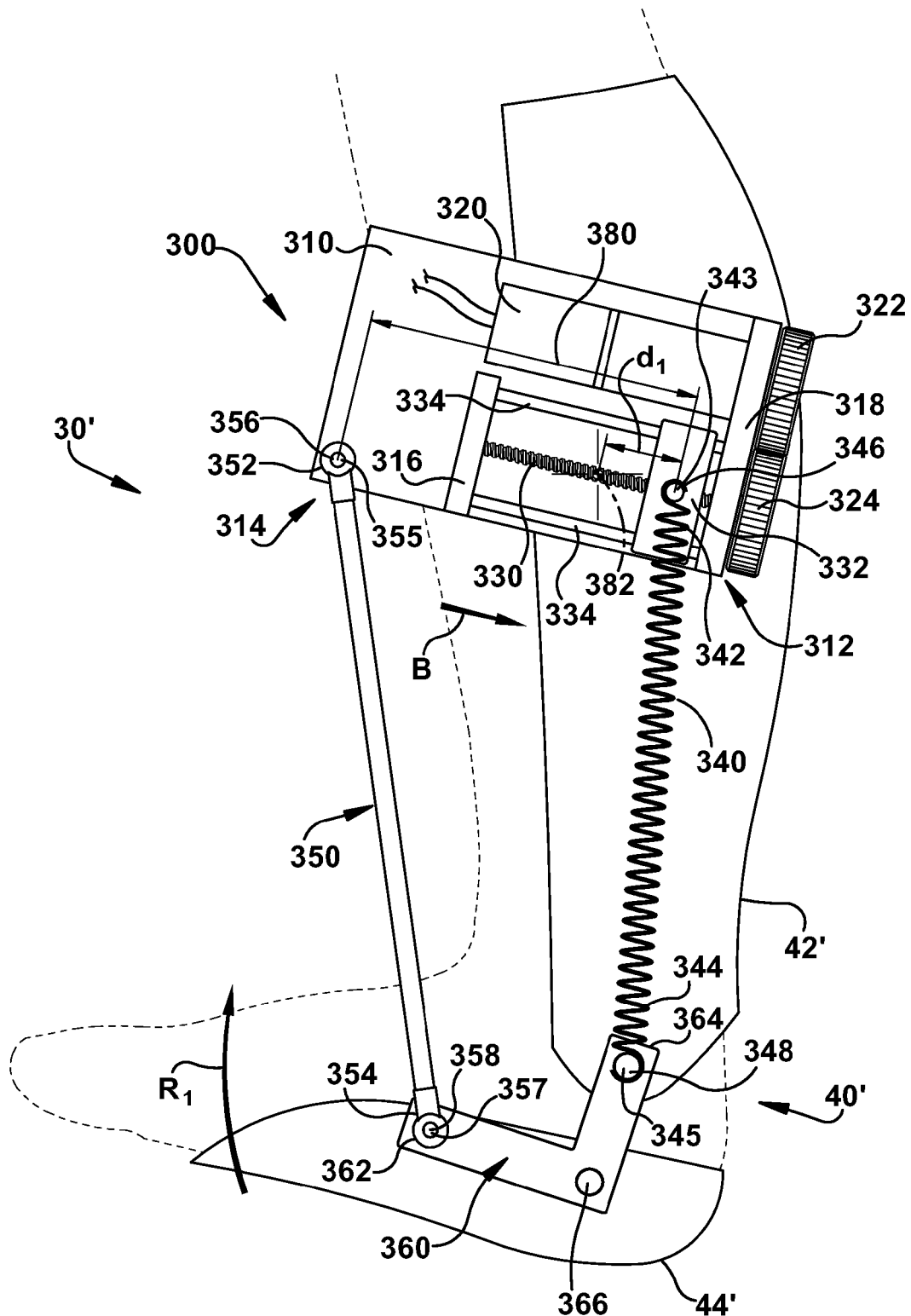
FIG. 8 is schematic illustration of the orthotic brace of FIG. 7 in a second condition.
Figure 9:
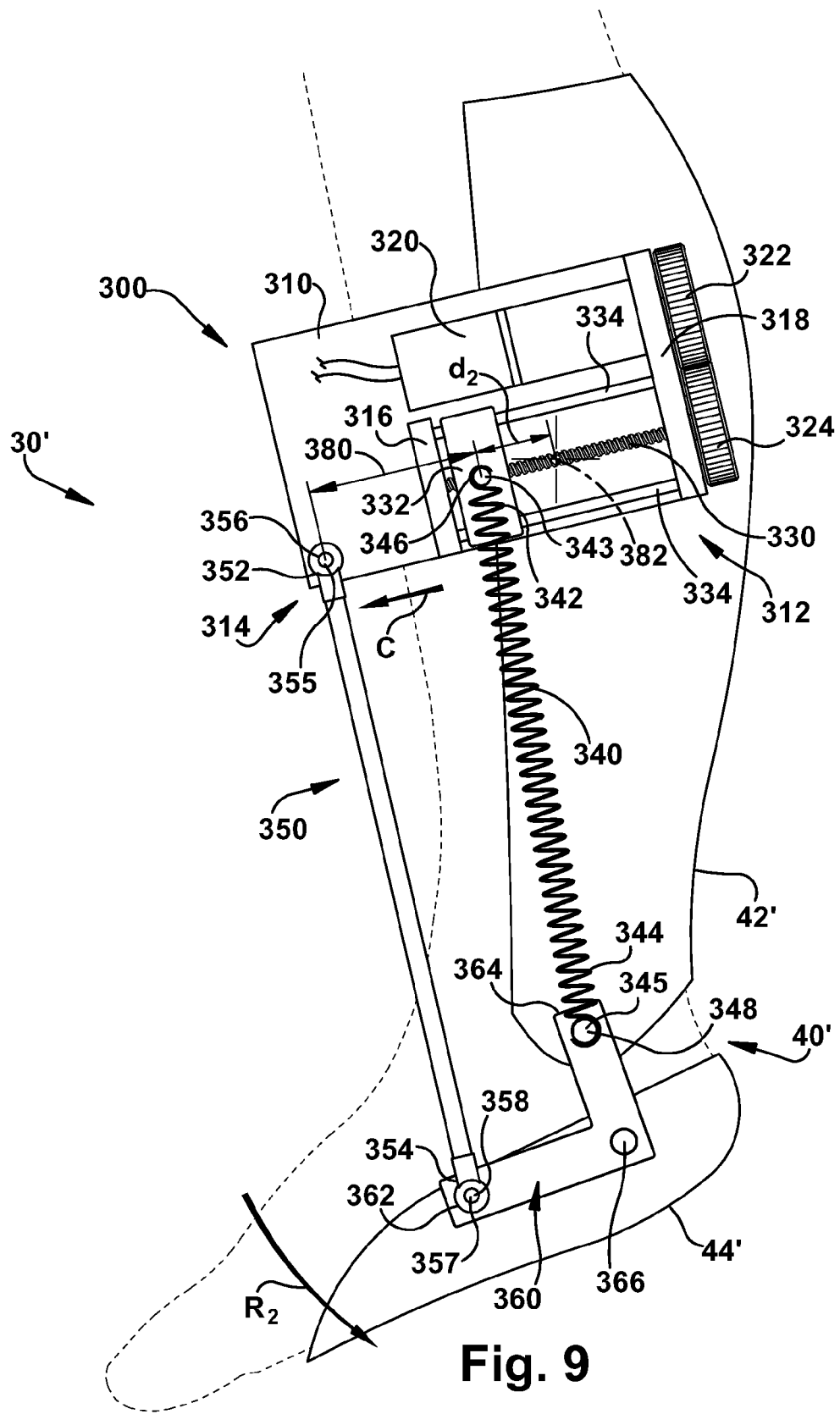
FIG. 9 is a schematic illustration of the orthotic brace of FIG. 7 in a third condition.

FIGS. 7-9 illustrate an orthotic brace 30' for providing dorsiflexion and plantar flexion assistance to the ankle of a user during walking by varying the resistance to movement between portions of the orthotic brace. The orthotic brace 30' includes a bracing device 40' in combination with a mechanism 300. The bracing device 40' includes a first portion 42' and a second portion 44' movable relative to one another. In FIG. 7, the orthotic brace 30' includes a two-part brace 40' for an ankle joint in which the first portion 42' is attached by straps with hook-and-loop releasable fasteners, for example, to the calf of an individual and the second portion 44' is similarly attached to the underside of the foot. The first portion 42' of the bracing device 40' is thus attached to a user on one side of the ankle joint and the second portion 44' is attached to the user on the opposite side of the ankle joint. Alternatively, the brace 30' may be configured for use with other joints of the individual, such as the elbow, shoulder, knee, etc. in which the portions 42', 44' of the bracing device 40' are secured to the first and second body members, respectively, of the joint.

The mechanism 300 includes a base plate 310 that has a first end 312 and a second end 314. The base plate 310 is secured to the first portion 42' of the bracing device and is pivotable relative to the first portion 42' about a pin or shaft defining a pivot point 382. The base plate 310 may pivotable relative to the first portion 42' via a bearing or slip-fit connection (not shown) or other conventional means.

A mounting plate 318 is secured to the first end 312 of the base plate 310 and a mounting plate 316 is secured closer to the second end 314 of the base plate than the first end. A motor 320 secured to the base plate 310 is operable to rotate a gear 322 positioned on a side of the mounting plate 318 adjacent the first end 312 of the base plate 310. The motor 320 is connected to a power source (not shown), such as a battery, which may be mounted on the base plate 310. The gear 322 mates with a gear 324 that is fixed to a threaded rod 330 extending through the mounting plate 318 and terminating at the mounting plate 316. The threaded rod 330 is rotatably received in both mounting plates 316, 318 via bearings or the like. In this configuration, rotation of the gear 322 by the motor 320 in one direction causes the mating gear 324 and, thus, the threaded rod 330 to rotate in the opposite direction.

Two support rods 334 extend between the mounting plates 316, 318 and are rigidly secured to the mounting plates. Alternatively, linear bearings may be used instead of support rods 334. The support rods 334 extend substantially parallel to the threaded rod 330. The support rods 334 may be made of metal or other durable and high strength material. A sliding member 332 is configured for movement along and relative to the threaded rod 330 and the support rods 334. In particular, a portion of the sliding member 332 is threaded to receive the threaded rod 330 and other portions of the sliding member are unthreaded for slidably receiving the support rods 334. The portion of the sliding member 332 that receives the threaded rod 330 may include one or more nuts formed of a low-friction material, such as polyacetal, or a ball screw (not shown).

A force transmission element 340, such as a spring, connects the mechanism 300 to the first portion 42' of the bracing device 40'. In particular, the spring 340 includes a hooked first end 342 connected to a rivet or pin 343 on the sliding member 332 and a hooked second end 344 connected to a rivet or pin 345 on a driven link 360 secured between the first portion 42' and the second portion 44' of the bracing device 40'. The point at which the first end 342 of the spring 340 connects to the pin 343 on the sliding member 332 defines a pivot point 346 and the point at which the second end 344 of the spring connects to the pin 345 on the driven link 360 defines a pivot point 348. Although the spring 340 is rotatable about the pivot point 348 the second end 344 of the spring may be pivotally or rigidly secured to the pin 345. The spring 340 is a tension spring that continually applies a pulling force to the sliding member 332 in a direction towards the pivot point 348. In other words, connecting the spring 340 to the sliding member 332 and the driven link 360 places the spring in a stretched condition beyond equilibrium, wherein the force exerted by the spring upon the sliding member is governed by Hooke's Law ($F=k\Delta L$).

A transmission link 350 cooperates with the driven link 360 to connect the mechanism 300 to the second portion 44' of the bracing device 40'. In particular, the transmission link 350 includes a first end 352 pivotally secured a pin or shaft 355 on the base plate 310 defining a pivot point 356 adjacent the first end and a second end 354 pivotally secured to a pin or shaft 357 on the driven link 360 defining a pivot point 358 adjacent the second end.

The driven link 360 has an L-shaped configuration and includes a first end 362 and a second end 364. The shape of the driven link 360 may generally mimic the shape of the foot and ankle of the individual such that rotation of the driven link about the pivot point 348 mimics rotation of the foot about the ankle and relative to the calf during walking. The first end 362 of the driven link 360 is rigidly secured to the second portion 44' of the bracing device 40' while being pivotally secured to the second end 354 of the transmission link 350 at the pivot point 358 and a second end 364 pivotally secured to the first portion 42' of the bracing device 40' at the pivot point 348. A midpoint 366 of the driven link 360 may also be rigidly secured to the second portion 44' of the bracing device 40' for added stability. The driven link 360 and the second portion 44' of the bracing device 40' are rotatable together and relative to the first portion 42' of the bracing device about the pivot point 348.

Together, the first portion 42', base plate 310, transmission link 350, and driven link 360 define a four-link system in which the links move relative to one another about the pivot points 348, 356, 358, and 382. In this configuration, the first portion 42' of the bracing device 40' acts as the ground link and the base plate 310 acts as the drive link in the four-link system. The sliding member 332 and the spring 340 are attached to this four-link system 42', 310, 350 and act to impart a torque to the base plate 310, depending on the position of the sliding member, to control movement of the second portion 44' of the bracing device 40' relative to the first portion 42'.

The length of the base plate 310, transmission link 350, and driven link 360 are constant. Since the second end 344 of the spring 340 is fixed to the pivot point 348 and the first end 342 of the spring 340 translates with the sliding member 332 along the threaded rod 330, the length of the spring changes.

The sliding member 332 has an initial, neutral position substantially at the midpoint of the threaded rod 330, which corresponds with the position of the pivot point 382 of the base plate 310. In other words, when the sliding member 332 is in the neutral position, the first end 342 of the spring is aligned with the pivot point 382 of the base plate 310. In this position, the line of action of the pulling force of the spring 340 on the sliding member 332 passes through the pivot point 382 of the base plate 310 and, thus, no moment is imparted to the base plate 310 about the pivot point. As a result, the spring 340 does not impart a force or moment to any of the other links 350 or 360 in the four-link system 42', 310, 350, 360, thereby placing the four-link system in a force-neutral state. When the user of the orthotic brace 30' walks or otherwise moves the foot to which the orthotic brace is secured, the mechanism 300 does not provide any additional support or aid to movement. In other words, the second portion 44' of the bracing device 40' is free to move, i.e., pivot, relative to the first portion 42' without being resisted by the mechanism 300.

As shown in FIG. 8, when it is desirable to provide dorsiflexion assistance to the user, such as to counteract foot-drop, the motor 320 is actuated to cause the sliding member 332 to move in the direction indicated by arrow B towards the gears 322, 324. More specifically, the motor 320 is rotated in a first direction, such as clockwise, to turn the gear 322, which in turn causes counterclockwise rotation of the mating gear 324 and the threaded rod 330 secured to the gear 324. Counterclockwise rotation of the threaded rod 330 results in translational movement of the sliding member 332 in the direction B.

Moving the sliding member 332 from the neutral position and away from the pivot point 382 in the direction B causes the four-link system 42', 310, 350, 360 to move out of the force neutral state. As the sliding member 332 moves away from the pivot point 382 in the direction B, the first end 342 of the spring 340 likewise moves away from the pivot point. Since the line of action of the biasing force of the spring 340 is now spaced from the pivot point 382, the biasing force will impart a clockwise moment to the base plate 310 about the pivot point. In this condition, the spring 340 acts to drive the base plate 310, i.e., the drive link, of the four-link system 42', 310, 350, 360. The moment imparted to the base plate 310 will have a force component equal to the vertical force component of the spring 340 and a moment arm equal to the distance between the pivot point 382 and the first end 342 of the spring, indicated by $d_1$.

The moment causes the base plate 310 to rotate clockwise about the pivot point 382, causing the transmission link 350 to move upwards (as viewed in FIG. 8) and pivot relative to the base plate about the pivot point 356. When the base 310 rotates about the pivot point 382, the first end 342 of the spring 340 is moved closer to the second end 344. The mechanism 300 is configured, however, such that the spring 340 is still in an expanded condition beyond equilibrium regardless of the final position of the first end 342 of the spring due to clockwise rotation of the base plate 310. Therefore, the spring 340 always exerts a non-zero force upon the sliding member 332.

Upward movement of the transmission link 350 causes the driven link 360 to pivot clockwise, i.e., upward, about the pivot point 348 on the first portion 42' of the bracing device 40'. Since the driven link 360 is secured to the second portion 44' of the bracing device 40', upward pivotal movement of the driven link likewise causes upward pivotal movement of the second portion of the bracing device in the manner indicated by $R_1$. Pivoting the second portion 44' of the bracing device 40' in this manner causes the toes of the user, which are held within the second portion, to pivot about the ankle upwards towards the leg, thereby assisting the user in dorsiflexion movement during walking.

In other words, moving the sliding member 332 in the direction B causes the second portion 44' of the bracing device 40' to move in the direction $R_1$ relative to the first portion 42' under the influence of the spring 340 acting on the base plate 310, i.e., drive link, of the four-link system 42', 310, 350, 360. The force of the spring 340 thereby provides resistance to movement of the second portion 44' of the bracing device 40' relative to the first portion 42' in a direction opposite to the direction $R_1$ to prevent foot-drop. It is this resistance that damps the foot's rotation downward and towards the ground after the heel contacts the ground during walking. When dorsiflexion assistance is no longer needed, the motor 320 is actuated in the opposite, i.e., counterclockwise, direction to cause the sliding member 332 to move back to the pivot point 382 and place the mechanism 300 back into the force neutral position in which no resistance to movement of the bracing portions 42', 44' is provided.

As shown in FIG. 9, when it is desirable to provide plantar flexion assistance to the user, such as to improve toe-off, the motor 320 is actuated to cause the sliding member 332 to move in the direction indicated by arrow C away from the gears 322, 324. More specifically, the motor 320 is rotated counterclockwise to turn the gear 322, which in turn causes clockwise rotation of the mating gear 324 and the threaded rod 330 secured to the gear 324. Rotating the threaded rod 330 in the clockwise direction results in translational movement of the sliding member 332 in the direction C.

Moving the sliding member 332 from the neutral position and away from the pivot point 382 in the direction C causes the four-link system 42', 310, 350, 360 to move out of the force neutral state. As the sliding member 332 moves away from the pivot point 382 in the direction C, the first end 342 of the spring 340 likewise moves away from the pivot point. Since the line of action of the biasing force of the spring 340 is now spaced from the pivot point 382, the biasing force will impart a counterclockwise moment to the base plate 310 about the pivot point. The moment will have a force component equal to the vertical force component of the spring 340 and a moment arm equal to the distance between the pivot point 382 and the first end 342 of the spring, indicated by $d_2$.

The moment causes the base plate 310 to rotate counterclockwise about the pivot point 382, causing the transmission link 350 secured thereto to move downwards (as viewed in FIG. 9) and pivot relative to the base plate about the pivot point 356. When the base 310 rotates about the pivot point 382, the first end 342 of the spring 340 is moved closer to the second end 344. The mechanism 300 is configured, however, such that the spring 340 is still in an expanded condition beyond equilibrium regardless of the final position of the first end 342 of the spring due to counterclockwise rotation of the base plate 310. Therefore, the spring 340 always exerts a non-zero force upon the sliding member 332.

Downward movement of the transmission link 350 causes the driven link 360 to pivot counterclockwise, i.e., downward, about the pivot point 348 on the first portion 42' of the bracing device 40'. Since the driven link 360 is secured to the second portion 44' of the bracing device 40', the downward pivotal movement of the ground link likewise causes downward pivotal movement of the second portion of the bracing device in the manner indicated by $R_2$. Pivoting the second portion 44' of the bracing device 40' in this manner causes the toes of the user, which are held within the second portion, to pivot downwards away from the leg, thereby assisting the user in plantar flexion movement during walking.

In other words, moving the sliding member 332 in the direction C causes the second portion 44' of the bracing device 40' to move in the direction $R_2$ relative to the first portion 42' under the influence of the spring 340 acting on the base plate 310, i.e., drive link, of the four-link system 42', 310, 350, 360. The force of the spring 340 thereby provides resistance to movement of the second portion 44' of the bracing device 40' relative to the first portion 42' in a direction opposite to the direction $R_2$. It is this resistance that dampens the foot's rotation upward and away from the ground to ensure a greater toe-off force during walking. When plantar flexion assistance is no longer needed, the motor 320 is actuated in the opposite, i.e., clockwise, direction to cause the sliding member 332 to move back to the pivot point 382 and place the mechanism 300 back into the force neutral position.

The amount of dorsiflexion or plantar flexion assistance provided by the mechanism 300 is dictated by the length of the respective moment arms $d_1$, $d_2$ and the force of the spring 340. As the sliding member 332 moves farther from the pivot point 382 in the direction B or C, the respective moment arm $d_1$ or $d_2$ of the tensioning spring 340 increases until the sliding member reaches the end of travel along the threaded rod 330. Therefore, the mechanism 300 of the present invention may provide any amount of dorsiflexion or plantar flexion assistance, i.e., resistance to movement of the second portion 44' relative to the first portion 42' in the counterclockwise and clockwise directions, respectively, by moving the sliding member 332 to the appropriate distance $d_1$ or $d_2$ from the pivot point 382.

In other words, when providing dorsiflexion assistance, the sliding member 332 may be placed in alignment with the pivot point 382 to place the four-link system 42', 310, 350, 360 in the force neutral condition corresponding with the fully unlocked condition, at the maximum allowable distance $d_1$ from the pivot point 382 in the direction B corresponding with a condition providing maximum resistance to foot-drop, or at any distance between the pivot point 382 and the maximum distance $d_1$ corresponding with a condition providing a non-zero resistance to foot-drop that is less than the maximum resistance.

Likewise, when providing plantar flexion assistance, the sliding member 332 may be placed in alignment with the pivot point 382 to place the four-link system 42', 310, 350, 360 in the force neutral condition corresponding with the fully unlocked condition, at the maximum allowable distance $d_2$ from the pivot point 382 in the direction C corresponding with a condition providing maximum resistance upward rotation of the foot, or at any distance between the pivot point 382 and the maximum distance $d_2$ corresponding with a condition providing a non-zero resistance to upward rotation of the foot that is less than the maximum resistance.

In order to tailor particular design and assistance criterion, the maximum length of travel of the sliding member 332 in each of the directions B and C from the pivot point 382 may be modified. Alternatively or additionally, a spring 340 with a particular spring constant may be chosen to increase or decrease the amount of assistance provided by the mechanism 300.

Figure 10:
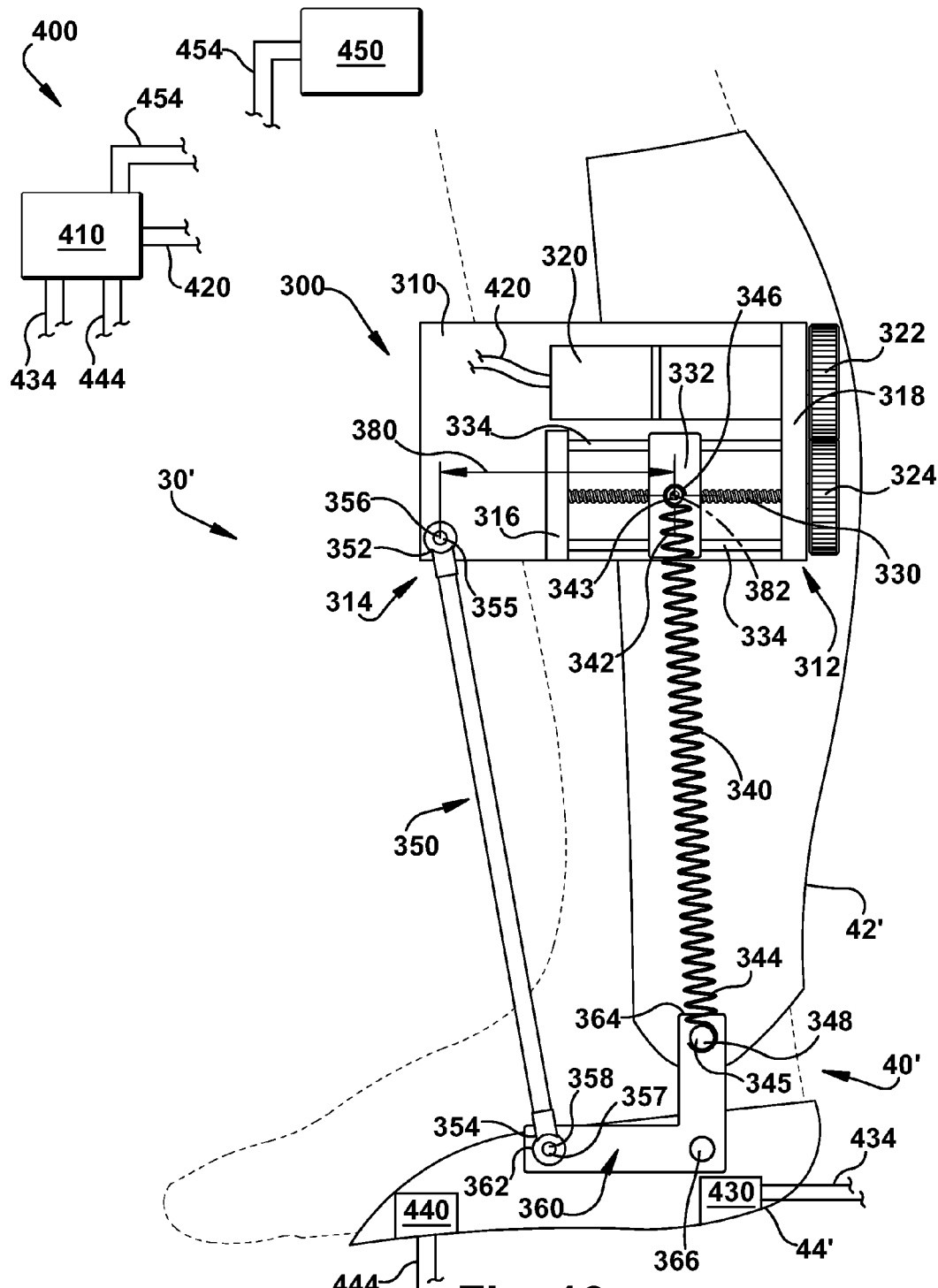
FIG. 10 is a schematic illustration of a control system in use with the orthotic brace of FIG. 7.

FIG. 10 illustrates a control system 400 for use with the orthotic brace 30' to provide dorsiflexion and plantar flexion assistance in real-time in accordance with the present invention. The control system 400 includes a controller 410 comprising a microprocessor and/or memory device. Such a controller 410 may be mounted on either the first portion 42' or the second portion 441 of the orthotic brace 30' or mounted or carried separately by the wearer with a wired or wireless connection 420 to the motor 320.

The controller 410 is also in electrical communication with a series of sensors for monitoring movement of the individual in order to control movement of the orthotic brace 30'. In particular, a pair of force sensing resistors (FSR) 430, 440 is secured to the second portion 44' of the bracing device 40'. One FSR 430 is secured to the second portion 44' at a position associated with the heel of the individual, i.e., the rearward end of the second portion as viewed in FIG. 10. The other FSR 440 is secured to the second portion 44' at a position associated with the toes of the individual, i.e., the forward end of the second portion. One or more wires 434 electrically connect the heel FSR 430 with the controller 410 and one or more wires 444 electrically connect the toe FSR 440 with the controller. The FSRs 430, 440 indicate which part of the foot is on the ground by detecting the change in reaction forces applied to the heel and the toes, respectively, by the ground.

One or more third sensors 450 are secured to the individual in a position that allows the sensor to detect the hip angle of the foot. The sensor 450 may, for example, be positioned on either of the bracing portions 42', 44' or elsewhere on the individual. One or more wires 454 electrically connect the heel sensor 450 with the controller 410. The sensors 450 determine whether the hip is anterior or posterior.

Before the orthotic brace 30' can function, the position of the sliding member 332 must be calibrated its encoder (not shown), as an encoder's position is not fixed as on a potentiometer. The sliding member 332 is calibrated by moving the sliding member to the neutral position, i.e., aligned with the pivot point 382, where there is no torque about the ankle. This alignment triggers an optical switch (not shown). Once the sliding member 332 is placed in the neutral position, the mechanism 300 will react to the user's needs via a feedback loop system.

The orthotic brace 30' will start to assist the user once movement of the legs is detected from standing by the FSRs 430, 440 and the sensor 450. In particular, the controller 410 communicates with the FSRs 430, 440 via the wires 434, 444 and with the sensor 450 via the wires 454 to detect motion of the orthotic device 30' and, thus, motion of the foot and calf of the user. The controller 410 reacts to the signals sent by the sensors 430, 440, 450 and actuates the motor 320 to move the slider member 332 in the direction B to assist the leg in swing with toe-drag by moving until the sensors sense a heel strike. At that time, the controller 410 will reverse rotation of the motor 320 to begin movement of the slider member 332 towards the neutral position to dampen toe-slap. Once the sensors 430, 440, 450 detect that the heel is leaving the floor, the controller 410 actuates the motor 320 to move the slider member 332 in the direction C to assist the leg with toe off. This will repeat until the subject stops walking.

Although the invention has been described as a single orthotic brace 30', a brace having a control system 400 may be provided for each leg in order to assist movement of both the user's feet and ankles during walking.

From the above description of the invention, those skilled in the art will perceive improvements, changes, and modifications. Such improvements, changes, and modifications are intended to be covered by the appended claims.

Having described the invention, the following is claimed:

1. An orthotic brace for a joint comprising:
   a bracing device having first and second portions movable relative to one another; and
   a mechanism having an actuator for placing the bracing device in a first condition in which the first portion has a first resistance to movement relative to the second portion and a second condition in which the first portion has a second, different resistance to movement relative to the second portion, the mechanism being capable of placing the bracing device in a third condition in which the first portion has a third resistance to movement relative to the second portion that is between the first and second resistance.

2. The orthotic brace of claim 1 wherein the first portion of the bracing device is adapted to be secured to a first member of the joint and the second portion of the bracing device is adapted to be secured to a second member of the joint.

3. The orthotic brace of claim 2 wherein the first member of the joint is a foot and the second member of the joint is a leg.

4. The orthotic brace of claim 1 wherein the mechanism comprises a plurality of force transmission elements positioned between the first and second portions of the bracing device, the mechanism varying the frictional forces between the force transmission elements to place the bracing device in at least one of the first, second, and third conditions.

5. The orthotic brace of claim 4 wherein the force transmission elements interlock with one another.

6. The orthotic brace of claim 4 wherein the force transmission elements mate with one another.

7. The orthotic brace of claim 4 wherein the force transmission elements are separated by a material that resists relative rotation between force transmission elements.

8. The orthotic brace of claim 4 wherein a force restoring element extends through the force transmission elements to vertically align the force transmission elements while the mechanism places the bracing device in at least one of the first, second, and third conditions.

9. The orthotic brace of claim 4 wherein a cable extends between the first portion of the bracing device and the actuator, the actuator tensioning the cable to adjust the distance between the first and second portions of the bracing device in order to vary the frictional forces between force transmission elements.

10. The orthotic brace of claim 9 wherein the cable extends through the force transmission elements.

11. The orthotic brace of claim 4 wherein the mechanism provides for a plurality of degrees of freedom of movement of the bracing device.

12. The orthotic brace of claim 1 wherein when the bracing device is in the first condition the first portion moves substantially resistance free relative to the second portion, the first portion of the bracing device being locked relative to the second portion when the bracing device is in the second condition.

13. The orthotic brace of claim 1 wherein the mechanism includes a linkage system connected between the first and second portions of the bracing device.

14. The orthotic brace of claim 13, wherein the mechanism includes an elastic member connected to the linkage system and movable from a first position for placing the bracing device in the first condition to a second position for placing the bracing device in the second condition.

15. The orthotic brace of claim 14 wherein when the elastic member is in the first position the first portion moves substantially resistance free relative to the second portion.

16. The orthotic brace of claim 14, wherein the elastic member has a first end connected to a fixed point on the bracing device and a second end connected to an axially movable sliding member for moving the elastic member between the first and second positions.

17. An orthotic brace for a joint comprising:
a bracing device having first and second portions movable relative to one another; and
a mechanism for placing the bracing device in a first condition in which the first portion has a first resistance to movement relative to the second portion and a second condition in which the first portion has a second, different resistance to movement relative to the second portion, the mechanism being capable of placing the bracing device in a third condition in which the first portion has a third resistance to movement relative to the second portion that is between the first and second resistance, the mechanism comprising
a universal joint assembly having first and second portions movable relative to one another, the first portion being connected to the first portion of the bracing device and the second portion being connected to the second portion of the bracing device; and
a sleeve movable relative to the universal joint assembly from a first position for placing the bracing device in the first condition to a second position for placing the bracing device in the second condition.

18. An orthotic brace for a joint comprising:
a bracing device having first and second portions movable relative to one another; and
a mechanism for placing the bracing device in a first condition in which the first portion has a first resistance to movement relative to the second portion and a second condition in which the first portion has a second, different resistance to movement relative to the second portion, the mechanism being capable of placing the bracing device in a third condition in which the first portion has a third resistance to movement relative to the second portion that is between the first and second resistance, the mechanism comprising:
first and second brackets integral with the first and second portions of the bracing device;
a plurality of force transmission elements positioned between the first and second brackets;
a cable extending through the force transmission elements and secured to one of the first and second brackets;
an actuator connected to the cable for adjusting the distance between the first and second brackets to vary the compressive force upon the force transmission elements in order to place the bracing device in at least one of the first, second, and third conditions.

19. An orthotic brace for a joint comprising:
a bracing device having first and second portions movable relative to one another; and
a linkage system for placing the bracing device in a first condition in which the first portion has a first resistance to movement relative to the second portion and a second condition in which the first portion has a second, different resistance to movement relative to the second portion, the linking system being capable of placing the bracing device in a third condition in which the first portion has a third resistance to movement relative to the second portion that is between the first and second resistance, the linkage system comprising:
a drive link pivotally connected to the second portion of the bracing device;
a driven link rigidly connected to the first portion of the bracing device and pivotally connected to the second portion of the bracing device;
a transmission link pivotally connected to the drive link and the driven link;
wherein an elastic member is connected to the linkage system, the elastic member having a first position in which the drive link does not impart a moment to the driven link and a second position in which the drive link imparts a moment to the driven link, the first position of the elastic member placing the bracing device in the first condition, the second position of the elastic member placing the bracing device in the second condition.

20. The orthotic brace of claim 17, wherein the first portion of the universal joint assembly is substantially cylindrical and the second portion of the universal joint assembly is tapered, the sleeve having a substantially cylindrical first portion movable over the first portion of the universal joint assembly and a tapered second portion that is movable over the second portion of the universal joint assembly.

21. The orthotic brace of claim 17, wherein the sleeve is connected to an actuator for moving the sleeve relative to the universal joint assembly between the first position and the second position.

* * * * *